United States Patent
Basu et al.

(10) Patent No.: US 9,804,142 B2
(45) Date of Patent: Oct. 31, 2017

(54) METHOD OF DETECTING THE EXTENT OF OIL DEGRADATION

(71) Applicant: Caterpillar Inc., Peoria, IL (US)

(72) Inventors: Amiyo K. Basu, Peoria, IL (US); R. Vinu, Chennai (IN); Anand Kumar Tripathi, Uttar Pradesh (IN)

(73) Assignee: Caterpillar Inc., Peoria, IL (US)

( * ) Notice: Subject to any disclaimer, the term of this patent is extended or adjusted under 35 U.S.C. 154(b) by 551 days.

(21) Appl. No.: 14/323,592

(22) Filed: Jul. 3, 2014

(65) Prior Publication Data

US 2016/0003794 A1 Jan. 7, 2016

(51) Int. Cl.
  *G01N 33/28* (2006.01)
  *G01N 27/26* (2006.01)
  *G01N 27/22* (2006.01)

(52) U.S. Cl.
  CPC ......... *G01N 33/2888* (2013.01); *G01N 27/26* (2013.01); *G01N 27/221* (2013.01)

(58) Field of Classification Search
  CPC .................................................. G01N 11/00
  USPC ............... 702/19, 20, 28, 30, 41, 57, 66, 77; 73/53.01
  See application file for complete search history.

(56) References Cited

U.S. PATENT DOCUMENTS

| | | |
|---|---|---|
| 4,169,768 A | 10/1979 | Bardasz |
| 5,914,890 A | 6/1999 | Sarangapani et al. |
| 6,553,812 B2 | 4/2003 | Park et al. |
| 7,581,434 B1 * | 9/2009 | Discenzo ........... G01N 33/2888 73/53.01 |
| 8,149,004 B2 | 4/2012 | Raju et al. |
| 8,234,915 B2 | 8/2012 | Schneider et al. |
| 8,704,174 B2 | 4/2014 | Ukon et al. |
| 2008/0119374 A1 * | 5/2008 | Willberg ................. C09K 8/52 507/209 |

(Continued)

FOREIGN PATENT DOCUMENTS

EP 2535708 A1 12/2012

OTHER PUBLICATIONS

Putintsev et al., Structure of Matter and Quantum Chemistry, The Molar Polarization and Refractio on Substances, 2006, Murmansk State Technical University, Murmans Russia, Russian Journal of Physical Chemistry, 2006, vol. 12, pp. 1949-1952.*

(Continued)

*Primary Examiner* — Alexander Satanovsky
*Assistant Examiner* — Felix Suarez
(74) *Attorney, Agent, or Firm* — Miller, Matthias & Hull LLP; Stephen K. Sampson

(57) ABSTRACT

A method of detecting the extent of degradation of an oil is provided. The method may comprise the steps of analyzing samples of the oil when fresh and when used; calculating electrochemical property data of the fresh and used engine oil; determining whether the electrochemical property data correlates with the degradation marker data; and using the electrochemical property to detect the extent of degradation of the oil of a used sample of the oil. The method may be used for any suitable oil, including mineral oil, synthetic oil and blends (a.k.a. semi-synthetic). The method can be used to maximize oil usage by monitoring used oil quality over time so that the oil is replaced when necessary and not before. The method can also identify trends in oil degradation.

4 Claims, 6 Drawing Sheets

(56) References Cited

U.S. PATENT DOCUMENTS

2010/0077656 A1* 4/2010 Yuen .................. C10L 1/14
    44/451
2012/0229151 A1   9/2012 Katafuchi

OTHER PUBLICATIONS

Juliusz B Gajewski et al.,"Correlation between electrical, mechanical and chemical properties of fresh and used aircraft engine oils", Journal of Physics: Conference Series, Jun. 23, 2011, vol. 301, No. 1, Institute of Physics Publishing, Bristol, GB.

Basu A. et al., "Smart sensing of oil degradation and oil level measurements in gasoline engines", SAE Technical Paper Series, Mar. 6, 2000, pp. 1-07, Society of Automotive Engineers, Warrendale, PA, US.

Zhu et al., "Survey of lubrication oil condition monitoring, diagnostics, and prognostics techniques and systems", Technical Program for MFPT 2012, Jul. 2013, vol. 2, Iss. 3, pp. 100-115, Journal of Chemical Science and Technology/The World Academic Publishing Co., Limited, Hong Kong.

* cited by examiner

Electrical properties of aged oil samples

| Time, hr | Density at 40°C, g cc$^{-1}$ | Molar volume, cc mol$^{-1}$ | Dielectric constant at 1 MHz | Molar polarization, cc mol$^{-1}$ | $\delta_p$ | TAN, mg KOH /g | Polarizability, × 10$^{-35}$ C$^2$ cm$^2$ J$^{-1}$ | Polarizability volume, × 10$^{-23}$ cc |
|---|---|---|---|---|---|---|---|---|
| 0 | 0.8646 | 411.65 | 2.23 | 119.70 | 0.5783 | 1.63 | 3.90 | 3.503 |
| 100 | 0.8661 | 410.93 | 2.25 | 120.86 | 0.7124 | 3.16 | 3.24 | 2.911 |
| 200 | 0.8668 | 410.60 | 2.29 | 123.47 | 0.825 | 3.13 | 2.64 | 2.375 |
| 300 | 0.8675 | 410.27 | 2.37 | 128.62 | 0.2234 | 4.61 | 5.47 | 4.912 |
| 400 | 0.8681 | 409.99 | 2.41 | 131.08 | 0.7611 | 4.00 | 3.40 | 3.055 |
| 470 | 0.8674 | 410.32 | 2.44 | 133.08 | 0.2646 | 4.10 | 5.58 | 5.014 |

*Average MW of oil = 355.91 g/mol, T = 40 °C*

FIG. 3

METHOD OF DETECTING THE EXTENT OF OIL DEGRADATION

TECHNICAL FIELD

This disclosure relates generally to a method of detecting the extent of engine oil degradation. More particularly, this disclosure relates to a method of detecting the extent of engine oil degradation by analyzing fresh and used oil samples to obtain degradation marker or other data, calculating electrochemical property data of the fresh and used oil, determining whether the electrochemical property data correlates with the degradation marker or other data, and using the electrochemical property data to detect the extent of engine oil degradation.

BACKGROUND

Engine lubricating oil generally comprises a base oil and additives. The base oil can be mineral oil (petroleum based oil), synthetic oil (non-petroleum based oil) or a blend of mineral and synthetic oils. The additives are chemical compounds added to the base oil to enhance the performance of the oil, and may include additives such as antioxidants, detergents, anti-wear agents, anti-rust agents and anti-foaming agents.

Lubricating oil degrades over time as the oil comes into contact with engine combustion byproducts and engine components. This degradation is the result of a number of physical phenomena. The additives become depleted. Foreign particles and soluble components mix with and contaminate the oil. The base oil molecules may react and combine to form heavier molecules, often causing the oil to darken and/or thicken. The oil molecules may undergo oxidation and nitration and may form acidic chemical compounds.

The type of engine oil, such as mineral, synthetic or blended (a.k.a. semi-synthetic), can have a significant effect on the formation and subsequent alteration of these chemical compounds. Additional factors such as ambient temperature, humidity, duty cycle and environmental conditions such as the presence of dust and dirt also play a role in the oil degradation process.

Currently, the condition of engine oil, i.e., when the useful life of the engine oil has ended, often is estimated by monitoring the length of time the oil has been in use or the distance travelled by the vehicle or machine, and modifying the estimate by taking into consideration the conditions under which the engine has been operating. The estimate is used to predict the interval, in time or mileage, between oil changes. However, the extent of engine oil degradation, i.e., the condition of the oil at any given time, may not be reliably detected by this method.

It would be useful to be able to detect the extent of oil degradation in used oil. The present disclosure addresses this need.

The present disclosure is directed toward a method of detecting the extent of oil degradation. Depending on the need, proactive action may be taken to avoid engine damage or failure.

SUMMARY OF THE DISCLOSURE

The disclosure relates to a method of detecting the extent of degradation of an oil. In one aspect the disclosure the method comprises the steps of:

analyzing samples of the oil when fresh and when used using an analytical technique to obtain degradation marker or other data;

calculating electrochemical property data of the fresh and used engine oil;

determining whether the electrochemical property data correlates with the degradation marker or other data; and if the electrochemical property data correlates with the degradation marker or other data, using the electrochemical property data of a used sample of the oil to detect the extent of degradation of the oil.

The method may be used for any suitable oil, including mineral oil, synthetic oil and blends (a.k.a. semi-synthetic). The method may be used to detect the extent of degradation in engine lubricating oils, gear oils, transmission oils and hydraulic oils.

The method can be used to maximize oil usage by monitoring used oil quality over time so that the oil is replaced when necessary and not before. The method can be used to determine whether used oil is still useable, thus saving on oil usage. The method can also identify trends in oil degradation.

BRIEF DESCRIPTION OF THE DRAWINGS

FIG. 3 shows electrical properties of aged oil samples over time for a selected oil.

DETAILED DESCRIPTION

Figure 1:
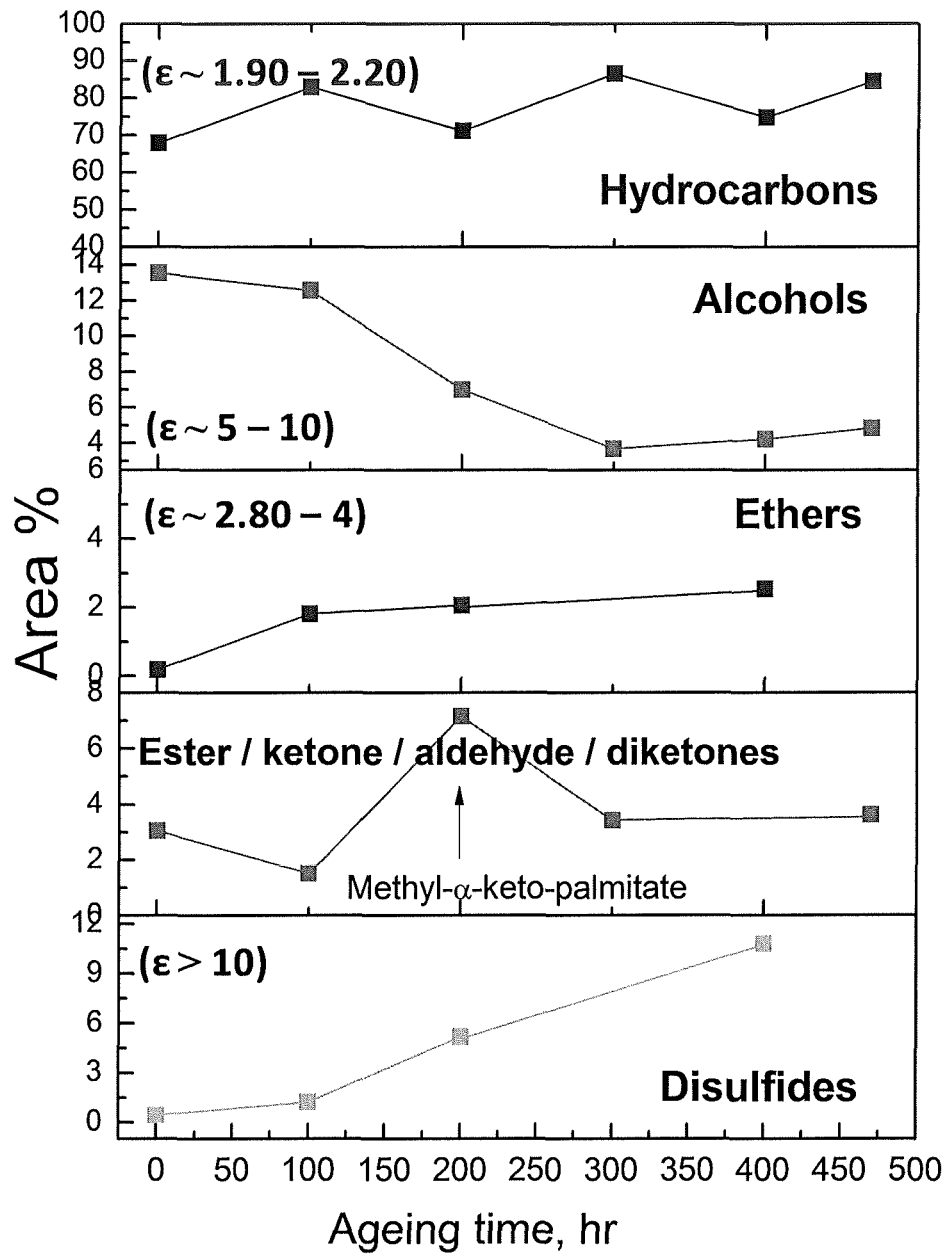
FIG. 1 a measurement over time for five functional groups in a selected used oil sample.

While this disclosure may be embodied in many forms, there is shown in the drawings and will herein be described in detail one or more embodiments with the understanding that this disclosure is to be considered an exemplification of the principles of the disclosure and is not intended to limit the disclosure to the illustrated embodiments.

For example, although the following discussion generally refers to a mineral oil, it should be understood that the disclosure also contemplates applications for any suitable oil, including mineral oil, synthetic oil and blends thereof. Also, although the following discussion generally refers to engine lubricating oil, it should be understood that the disclosure may relate to other oils containing additives, including but not limited to gear oil, transmission oil and hydraulic oils.

Engine lubricating oil degrades and degrades as the oil comes into contact with combustion byproducts and engine components. The oil molecules react (via oxidation, sulfation, nitration and other chemical processes) and combine to form acidic chemical compounds and to form heavier molecules, causing the oil to darken and thicken.

The degradation can be the result of normal engine use, degradation from engine failure, water contamination, fuel contamination, contamination due to unusual combustion by-products, and other types of contamination.

The present disclosure relates to a method of detecting the extent of oil degradation by (1) analyzing fresh and used oil samples to obtain degradation marker data, (2) calculating electrochemical property data (such as Hansen's polar parameter ($\delta_P$) and molar polarization ($P_m$)) of the fresh and used oil, (3) determining whether the electrochemical property data correlates with the degradation marker or other data, and if so, then (4) using the electrochemical property data to detect the extent of engine oil degradation.

Step 1—Analyzing Fresh and Used Oil Samples to Obtain Degradation Marker Data

The first step in detecting the extent of oil degradation is to analyze fresh and used samples of the oil to obtain degradation marker or other data and other data needed to calculate selected electrical properties of the oil. Degradation markers are those parameters that can be used to detect the extent of engine oil degradation. The degradation marker or other data can be the presence and concentration of certain chemical compounds, physical data and electrical data.

As the engine lubricating oil degrades, the fresh engine oil molecules react and combine, that is, are transformed (via oxidation, sulfation, nitration and other chemical processes) into other chemical compounds, including heavy hydrocarbons, alcohols, ethers, esters, ketones and diketones, aldehydes and disulfides and other functional groups that can serve as degradation marker for the purpose of detecting the state of the engine oil degradation. These transformations can be exacerbated in certain ambient conditions, for example, when engines are operated in dusty conditions.

For example, the chemical compounds that are the product of the transformation of the ethers in the fresh oil can include acetonyl-decyl and hexyl-octyl ethers. The chemical compounds that are the product of the transformation of the disulfides in the fresh oil can include dihexyl sulfide and dioctyl disulfide containing species of sulfion acids. The chemical compounds that are the product of the transformation of the alcohols in the fresh oil can include species of alcohols such as octyldodecan-1-ol, ethyl-1-decanol, 2-propyl-1-1decanol and 1-pentatcontanol.

The degradation markers may include, but are not limited to, chemical parameters, physical parameters and/or electrical parameters. Chemical parameters may include the presence and concentration of one or more functional groups of chemical compounds such as hydrocarbons, alcohols, ethers, esters, ketones and diketones, aldehydes and disulfides. The physical parameters may include the viscosity, Total Acid Number (TAN), Total Base Number (TBN), and the levels of nitration, sulfation, oxidation and hydration in the used oil.

The relevant functional groups can be identified by using, for example, mass spectrometry or infrared spectroscopy to determine which compounds in a selected oil sample change over time.

FIG. 1 is a graph of the concentration of five functional groups in a selected oil sample taken over time. In this particular sample, the concentration of hydrocarbons changes only slightly. The concentration of alcohols decreased. The concentrations of ethers and disulfides (dihexyl sulfide and dioctyl sulfide) were observed to increase over time. The total concentration of esters, ketones, aldehydes and diketones changed only slightly if at all. This data indicates that for this particular oil sample at least three functional groups (alcohols, ethers and disulfides) can be used as degradation markers to determine the extent of engine oil degradation.

Figure 2:
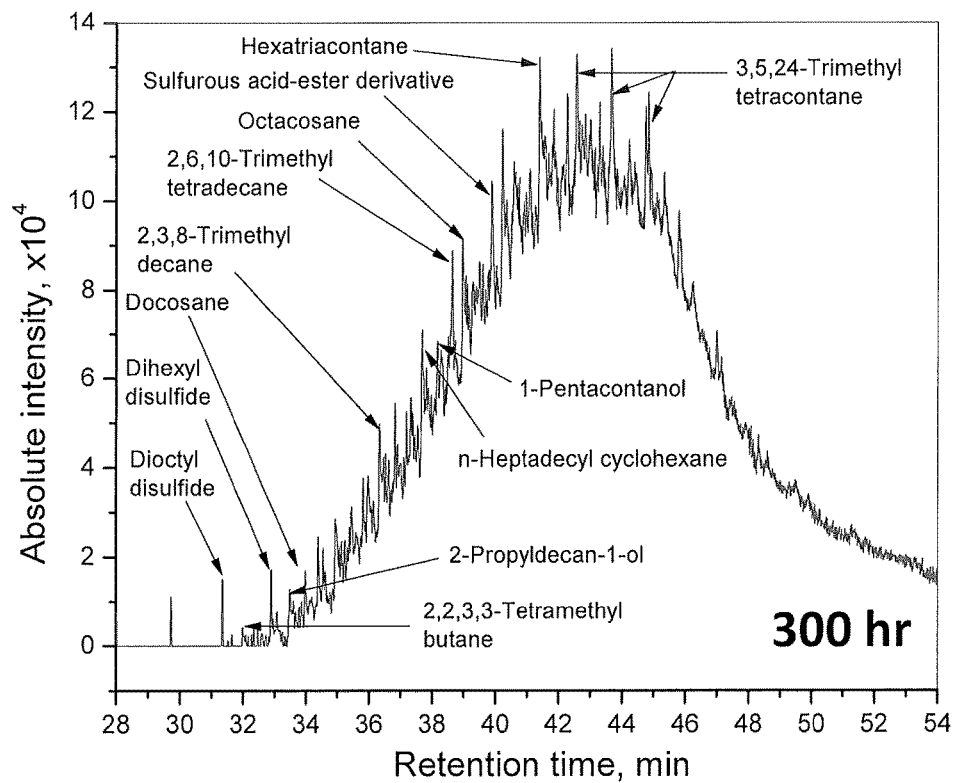
FIG. 2 is a printout of gas chromatography and mass spectrometry (GC and MS) data showing peak intensities of chemical compounds belonging to various functional groups found in used engine oil.

FIG. 2 is a chromatographic printout of gas chromatography and mass spectrometry (GC and MS) data showing "peak intensities" of chemical compounds belonging to various functional groups found in used engine oil. In the present method only some of these compounds may be selected as engine oil degradation markers.

In summary, the existence and concentration of various "transformed" functional groups can be used as markers to indicate the extent of engine oil degradation. The actual functional groups (markers) can change depending on the type of oil and the environment in which it is used.

Other types of degradation markers may be used, including physical parameters such as viscosity, TAN, TBN and the levels of nitration, sulfation, oxidation and hydration in the used oil.

Step 2—Calculating Electrochemical Property Data (Such as Polarity ($\delta_P$) and Molar Polarization ($P_m$)) of Fresh and Used Oil This step involves calculating electrochemical property data (such as Hansen's polar parameter ($\delta_P$) and molar polarization ($P_m$)) of fresh and used oil based on the analytical data collected during step 1. For example, Hansen's polar parameter ($\delta_P$) may be calculated using the following group additivity formula:

$$\delta_{p,oil} = \Sigma \delta_{p,i} \varnothing_i$$

where:
$\delta_{p,i}$=Hansen's polar parameter of polar species i
and $\varnothing_i$=relative volume of species i The Hansen's polar parameter values ($\delta_P$) for various organic compounds that may form during oil degradation is given below:

TABLE 1

| Organic Compound | Carbon No. | $\delta_p$ (J/cm$^3$)$^{1/2}$ |
|---|---|---|
| Alcohols | | |
| 2-OCTYLDODECAN-1-OL | 20 | 1.5176 |
| 1-DECANOL, 2-ETHYL | 12 | 2.4383 |
| 2-PROPYLDECAN-1-OL | 13 | 2.2664 |
| 1-PENTACONTANOL | 50 | 0.6281 |
| Ethers | | |
| ACETONYL DECYL ETHER | 14 | 3.6473 |
| HEXYL OCTYL ETHER | 14 | 1.6938 |
| Others (esters, carbonyls, sulfides) | | |
| LMETHYL-α-KETO PALMITATE | 17 | 5.5029 |
| DECANEDIOIC ACID, DIDECYL ESTER | 30 | 3.5065 |
| HEXANE,1-(HEXYLOXY)-4-METHYL | 13 | 1.8131 |
| DIHEXYL SULFIDE | 12 | 1.962 |

Alternatively, molar polarization ($P_m$) may be calculated using the following formula:

$$P_m = (MW/\rho)((\in_r -1)/(\in_r +2)) = (N_A/3\in_0)(\alpha + (\mu^2/3k_B T)$$

Where:
$P_m$=molar polarization/electrical dipole moment density, cc/mol.
MW=average molecular weight of the oil, g/mol
$\in_r$=dielectric constant of the oil
$\rho$=density of the oil, g/cc
$\in_o$=free space permittivity, 8.85418×10$^{-12}$ C$^2$/m-j
$N_A$=Avogadro's number, 6.023×10$^{23}$ mol$^{-1}$
$\alpha$=polarizability (c$^2$m$^2$/J)
$\mu$=dipole moment due to polar species in the oil, Debye
$k_B$=Boltzmann's constant, 1.131×10$^{-23}$ J/K
T=Temperature, K Step 3—Determining Whether the Electrochemical Property Data Correlates with the Degradation Marker or Other Data FIG. 3 shows values for Hansen's polar parameter ($\delta_P$) and molar polarization ($P_m$) of an oil sample over time and demonstrates that certain electrical properties (such as polarity ($\delta_P$)) correlate well with degradation marker or other data (such as TAN). It is theorized that an increase in TAN correlates to an increase in polarity due to the ionization of certain chemical species such as acids, sulfides and diketones present in aged oil. Thus, polarity can be used to detect the extent of oil degradation.

Figure 4:
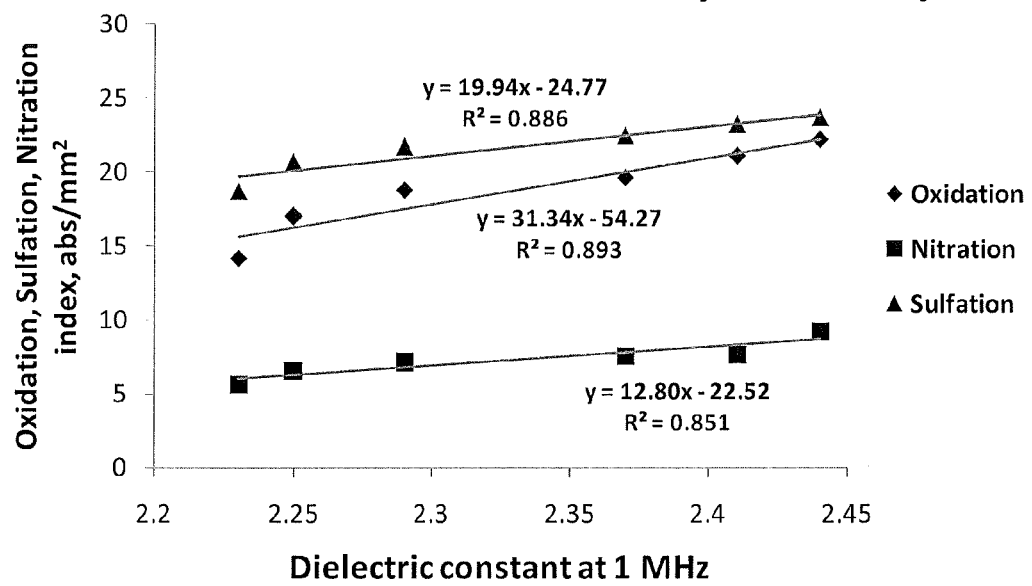
FIG. 4 shows the levels of oxidation, sulfation and nitration plotted against dielectric constant for a selected oil.

FIG. 4 shows the levels of oxidation, sulfation and nitration plotted against dielectric constant ($\in_r$). From this data it can be seen that the dielectric constant of the oil increases with degradation and correlates well with increases in levels of oxidation, sulfation and nitration. Thus, dielectric constant can be used to detect the extent of oil degradation.

Figure 5:
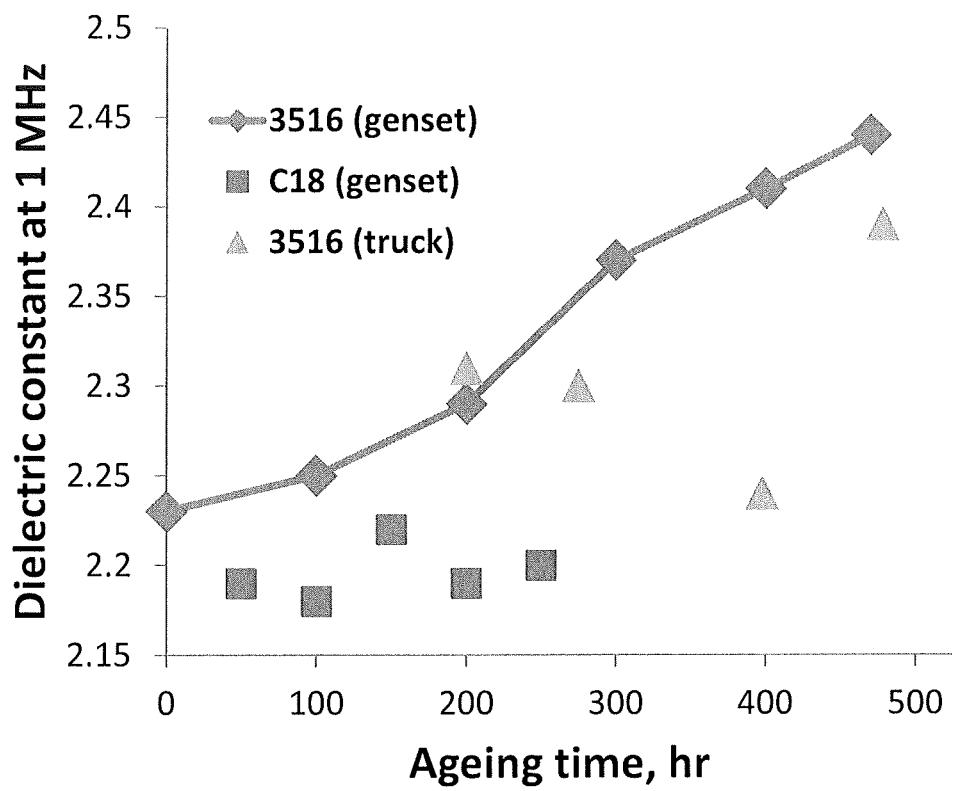
FIG. 5 shows dielectric constant over time for selected oils.

The same electrochemical property parameter may not be suitable to use for the detection of engine oil degradation in all oils. FIG. 5 shows dielectric constant over time for three selected oil samples, each data set represented by a geometric symbol: triangles, squares and diamonds. It can readily be seen that dielectric constant changes over time for the data set represented by diamonds but not for the other two data sets. Thus dielectric constant might be suitable to use to detect the extent of engine oil degradation for the oil represented by the set of diamonds but not for the other two oils.

Step 4—Using the Electrochemical Property Data to Detect the Extent of Engine Oil Degradation.

Once it has been established that certain electrochemical property data correlates with degradation marker or other data, the electrochemical property data can then be used to detect the extent of oil degradation. For example, a sample of a used oil can be taken in the field and analyzed for certain parameters, then the parameters used to calculate one or more electrical properties. The electrical properties then can be used to detect the extent of oil degradation.

Summary of Method

Figure 6:
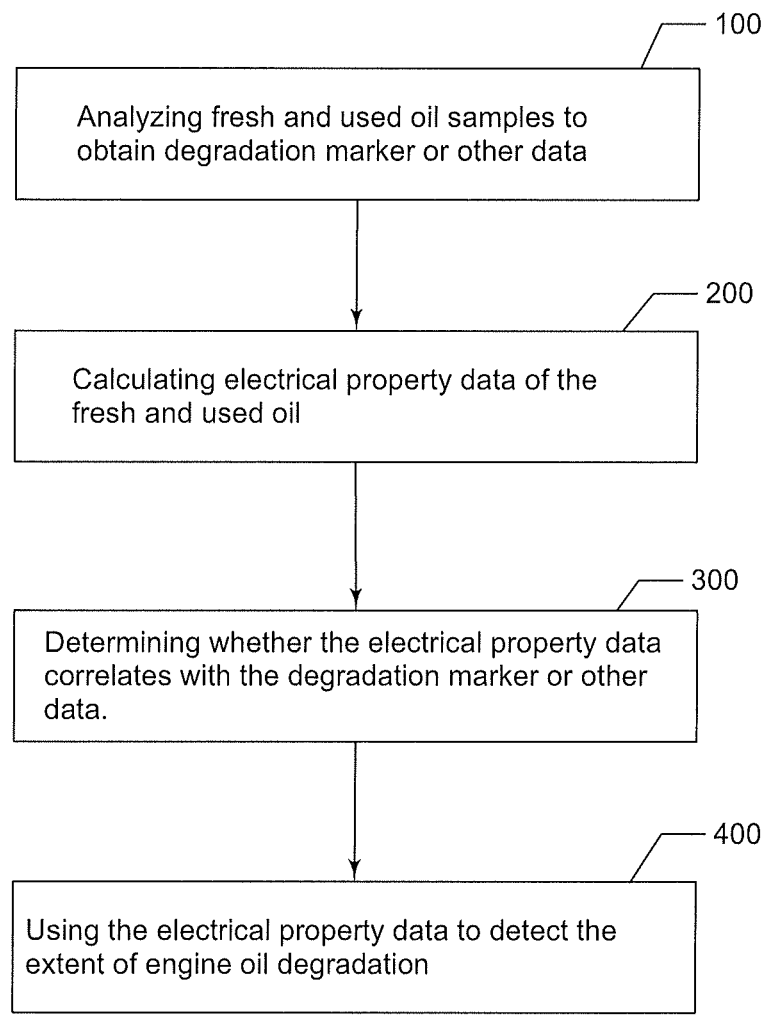
FIG. 6 is a schematic diagram of a method according to the present disclosure.

FIG. 6 is a schematic diagram of a method of detecting the extent of oil degradation according to the present disclosure. The method may comprise the following steps:

Step 100: Analyzing samples of the engine oil when fresh and when used using an analytical technique to obtain degradation marker or other data. The analytical technique may be selected from the group consisting of: (1) GC/MS (gas chromatography and/or mass spectrometry), wherein the degradation marker data comprises oil composition data, (2) TGA/DSC (thermogravimetric analysis/differential scanning calorimetry), wherein the degradation marker data comprises thermal stability data, (3) FT-IR (Fourier Transform Infrared Spectroscopy), wherein the degradation marker data comprises structural analysis data, (4) lubricant analysis, wherein the degradation marker data comprises TBN, nitration, sulfation, oxidation, moisture and/or glycol content data, (5) potentiometric titration, wherein the degradation marker data comprises TAN data, (6) wear metal analysis, wherein the degradation marker data comprises additive depletion data, and (7) viscosity and density analyzers, wherein the degradation marker data comprises viscosity, density and/or viscosity index.

Step 200: Calculating electrochemical property data (for example, polarity or molar polarization) of the fresh and used engine oil.

Step 300: Determining whether the electrochemical property data correlates with the degradation marker or other data (and thus the electrochemical property can be used as a new type of degradation marker).

Step 400: If the electrochemical property data correlates with the degradation marker data, using the electrochemical property of a used oil sample of engine oil to detect the extent of degradation of the engine oil. This step may involve taking an oil sample from a machine in the field, analyzing the oil sample for various properties, including those needed to calculate the electrochemical property of interest, calculating the electrochemical property of interest, and using the electrochemical property to decide whether to change the oil in the machine.

Other Findings and Conclusions

The increase in kinematic viscosity in aged oil samples correlates with an increase in the apparent activation energy of degradation. As the oil degrades, longer chain hydrocarbons are formed which increases kinematic viscosity.

With degradation, alcohol concentration decreases, ether and sulfide concentrations increase, and a range of (di)esters, carboxylic acids and di-carbonyl compounds was observed.

The increase in total acid number (TAN) correlates with an increase in the ionizability of species like acids, sulfides and diketones present in the aged oil.

The overall trend of ($\delta_P$) of the oil increased with degradation time. ($\delta_P$) was also utilized to find dipole moment and polarizability volume of the oil.

Molar polarization (induced+electric charge) of the oil was found to increase from 120 to 133 cc/mol. This is a clear indication that dielectric constant can be used as the sensing variable to detect polarization of engine oils with degradation.

INDUSTRIAL APPLICABILITY

The method of the present disclosure may be used whenever and wherever oil degradation is a problem. The method can apply to the construction industry, mining industry, aerospace industry, chemical industry, locomotive industry or any industry where oil degradation occurs. For example, in the construction industry oil degradation occurs in heavy duty off road machines, and the problem is exacerbated in dry dusty environments.

The method can be used to maximize engine oil usage by monitoring used oil quality over time so that engine oil is replaced when necessary and not before. The method can be used to determine whether used oil is still useable, thus saving on oil usage. The method can also identify trends in oil degradation.

It is understood that the embodiments of the disclosure described above are only particular examples which serve to illustrate the principles of the disclosure. Modifications and alternative embodiments of the disclosure are contemplated which do not depart from the scope of the disclosure as defined by the foregoing teachings and appended claims. It is intended that the claims cover all such modifications and alternative embodiments that fall within their scope.

The invention claimed is:

1. A method of detecting the extent of degradation of oil, the method comprising the steps of:

analyzing samples of a machine's oil supply when fresh and when used wherein the compounds within the oil supply are identified using a chemical compound measurement machine where compound changes are recorded as a function of time;

identifying at least one compound selected from the group consisting of alcohols that decrease by at least 1 area percent per 100 hours of machine operation, ethers that increase by at least 0.2 area percent per 100 hours of operation, and disulfides that increase by at least 0.5 area percent per 100 hours of operation as a degradation marker;

measuring a dielectric constant using an electrochemical property measurement machine where dielectric constant changes are recorded as a function of time;

selecting the dielectric constant as an oil degradation indicator when the dielectric constant correlates to the at least one degradation marker given at least a 0.02 dielectric constant increase per 100 hours of machine operation; and communicating the extent of oil degradation based on the dielectric constant if the degradation markers correlate with the dielectric constant as a function of time.

2. The method of claim 1 wherein using the electrochemical property data of a used sample of the oil to detect the extent of degradation of the oil comprises the steps of:

taking an oil sample from a machine in the field;

analyzing the oil sample for those properties needed to measure the electrochemical property data;

measuring the electrochemical property data; and using the electrochemical property data to decide whether to change the oil in the machine.

3. A method of detecting the extent of degradation of oil, the method comprising the steps of:

analyzing samples of a machine's oil supply when fresh and when used wherein the compounds within the oil supply are identified using a chemical compound measurement machine where compound changes are recorded as a function of time;

identifying at least one compound of a group consisting of alcohols that decrease by at least 1 area percent per 100 hours of machine operation, ethers that increase by at least 0.2 area percent per 100 hours of operation, and disulfides that increase by at least 0.5 area percent per 100 hours of operation as a degradation marker;

measuring a molar polarization using an electrochemical property measurement machine where molar polarization changes are recorded as a function of time;

selecting the molar polarization as an oil degradation indicator when the molar polarization correlates to the at least one degradation marker given at least a 1 cc mole$^{-1}$ molar polarization increase per 100 hours of machine operation; communicating the extent of oil degradation based on the dielectric constant if the degradation markers correlate with the dielectric constant as a function of time.

4. The method of claim 3 wherein using the electrochemical property data of a used sample of the oil to detect the extent of degradation of the oil comprises the steps of:

taking an oil sample from a machine in the field;

analyzing the oil sample for those properties needed to measure the electrochemical property data;

measuring the electrochemical property data; and using the electrochemical property data to decide whether to change the oil in the machine.

* * * * *